(12) United States Patent
Wong

(10) Patent No.: US 6,836,918 B1
(45) Date of Patent: Jan. 4, 2005

(54) ELECTRIC TOOTHBRUSH

(76) Inventor: Ying Kau Wong, Flat B, 9th Floor, Shun Tai Building, No. 4 Fuk Wa Street, Kowloon, Hong Kong (CN)

(*) Notice: Subject to any disclaimer, the term of this patent is extended or adjusted under 35 U.S.C. 154(b) by 170 days.

(21) Appl. No.: 10/119,575

(22) Filed: Apr. 10, 2002

(51) Int. Cl.$^7$ .............................................. A46B 13/00
(52) U.S. Cl. ........................... 15/22.1; 15/22.2; 15/22.4
(58) Field of Search ................................. 15/22.1, 22.2, 15/22.4, 28

(56) References Cited

U.S. PATENT DOCUMENTS

| | | | |
|---|---|---|---|
| 3,284,829 A | * | 11/1966 | Allen .......................... 15/22.1 |
| 3,978,852 A | * | 9/1976 | Annoni ........................ 601/142 |
| 4,710,995 A | * | 12/1987 | Joyashiki et al. ............. 15/22.1 |
| 5,359,747 A | * | 11/1994 | Amakasu .................... 15/22.1 |
| 5,467,494 A | | 11/1995 | Müller et al. |
| 5,617,601 A | | 4/1997 | McDougall |
| 5,617,603 A | | 4/1997 | Mei |
| 5,625,916 A | | 5/1997 | McDougall |
| 5,794,296 A | | 8/1998 | Wong |
| 6,178,579 B1 | * | 1/2001 | Blaustein et al. ............... 15/28 |
| 2002/0066147 A1 | * | 6/2002 | Schutz ........................ 15/22.1 |
| 2003/0084528 A1 | * | 5/2003 | Chan et al. .................. 15/22.1 |

* cited by examiner

*Primary Examiner*—Robert J. Warden, Sr.
*Assistant Examiner*—Laura C Cole
(74) *Attorney, Agent, or Firm*—Alix, Yale & Ristas, LLP

(57) ABSTRACT

An electric toothbrush is provided a cam mechanism and a crank mechanism in the handle. The cam mechanism comprises a cam, mounted on a rotary shaft of a motor via a frame; and a slave unit making a reciprocating movement, defined within the handle and engaged with the cam. The crank mechanism comprises a crank, mounted concentrically with the brush head; a link rod, jointed with the crank; and a block, defined within the brush body and engaged with the slave unit. Therefore, the structure of the electric toothbrush of the present invention is simplified, thus its cost can be reduced accordingly. In addition, the brush head of the present invention can be formed star shape or be inclined to improve the area of contact for super cleaning and be convenient for removing the deposit on the teeth.

23 Claims, 8 Drawing Sheets

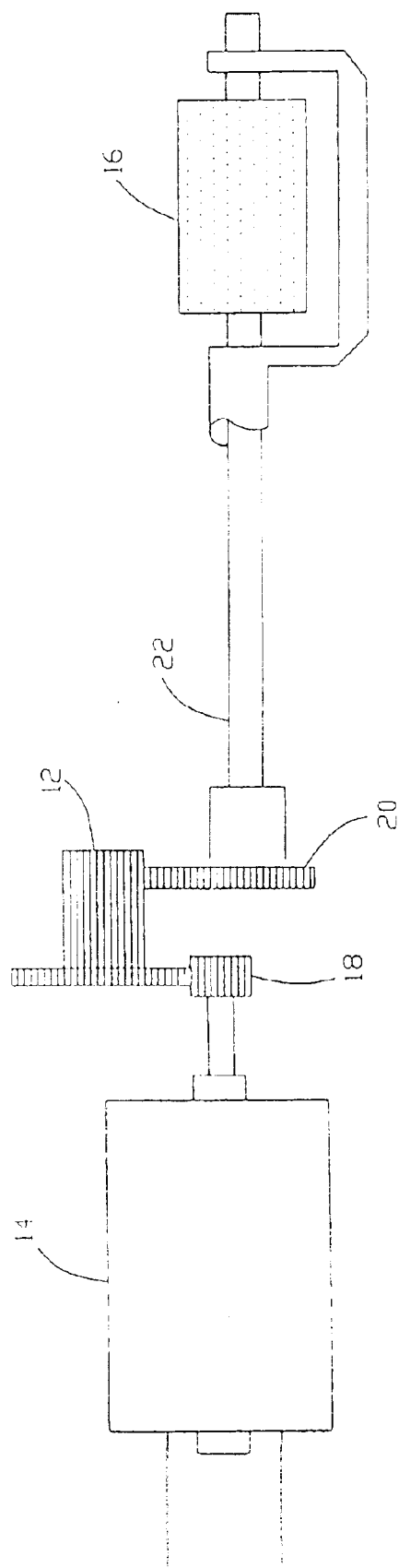

Fig. 2 Prior Art

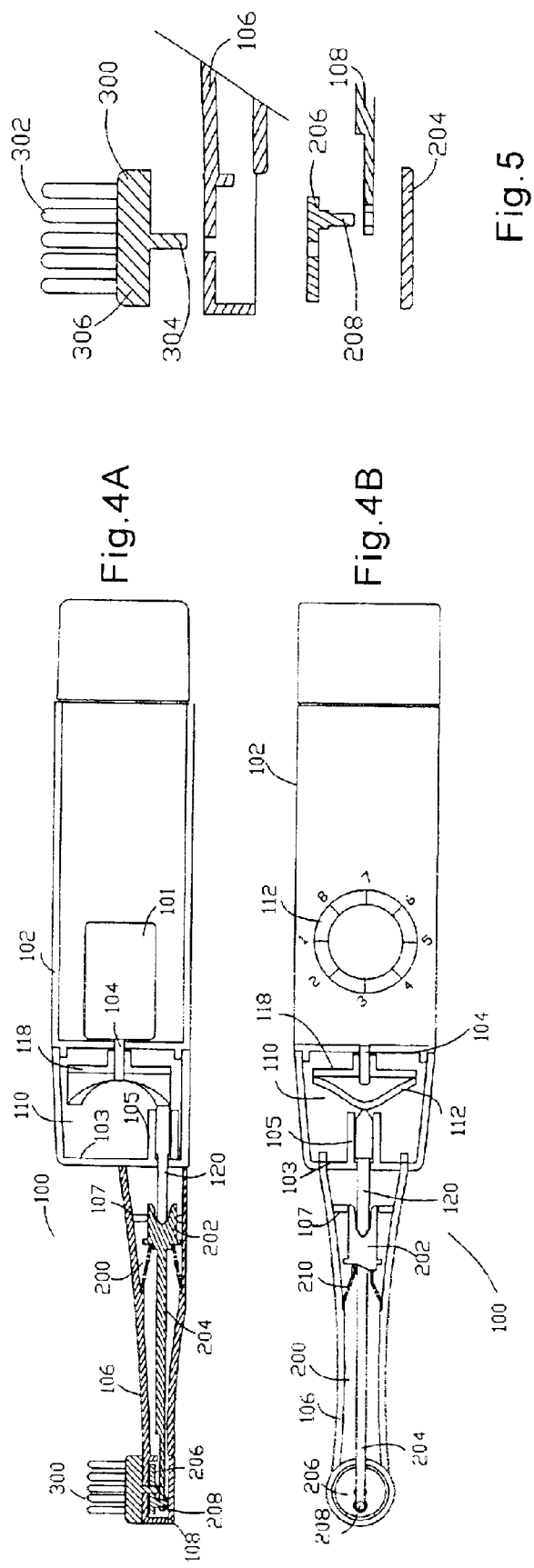

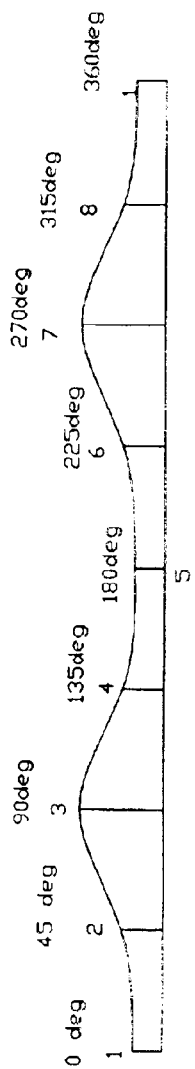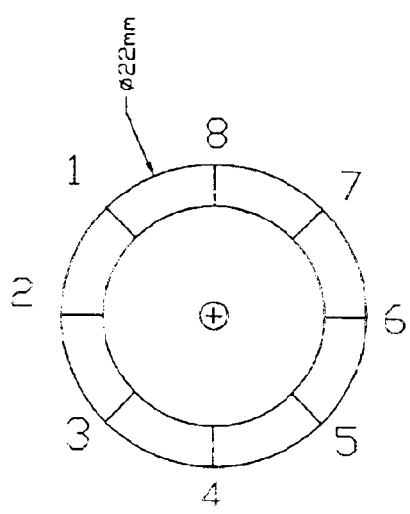
Fig. 7B
Fig. 7A

ELECTRIC TOOTHBRUSH

FIELD OF THE INVENTION

The present invention relates generally to electric toothbrushes, particularly to a toothbrush in which a cam mechanism and a crank mechanism are provided to make a brush head rotate.

BACKGROUND OF THE INVENTION

Equipped with a motorized driven member, an electric toothbrush is becoming popular in the present time, and many kinds of electric toothbrushes have been already on the market. Generally, the electric toothbrush of the prior art comprises a motor provided in a housing inside the handle and a transmission mechanism coupled with the shaft of motor. With the rotation of the motor, the transmission mechanism can drive the brush head. However, a gear driver system is usually applied to be a transmission mechanism. For example, U.S. Pat. No. 5,794,296 disclosed such a constitution, as shown in FIG. 1. Gear box 12 is provided as to be a transmission mechanism, that is, a master gear 18 is fixed on the shaft of motor 14; a equipment gear 20 is coupled with an axis 22 of brush head 16. However, the structure of such meshed gears is not only complex but inefficient as well. Further, the brush head 16 and its method of rotary is not as the same as that of the traditional brush tooth, thus user will feel inconvenient while using it.

FIG. 2 is another brush head of an electric brush tooth 2 of the prior art. Although plenty of groups of brush 22 are arranged on the head 24, the area for arranging the brush 22 is small, as the kind of brush head 24 has to clean the teeth one by one. Definitely, the turning angle of the head 24 and the area covered by the brush will determine whether the kind of electric brush tooth of the prior art can super clean the teeth. However, the turning angle for most of the electric brush of the prior art is very limited, generally less than 180 degrees. Furthermore, when the motor rotates 3 turns, the head 24 can be driven to make 1 cycle motion, so it is difficult to achieve the requirement of energy saving because of its inefficiency.

Summary of the Present Invention

An object of the present invention is to provide an electronic tooth brush having a cam mechanism and a crank mechanism inside a handle to achieve the rotary of the brush head.

Another object of the present invention is to provide an electric brush tooth in which the brush head is arranged eccentrically for super cleaning the teeth.

Another object of the present invention is to provide an electric brush tooth in which the brush head is arranged as an incline for super cleaning the teeth.

The toothbrush of the present invention overcomes the disadvantages of conventional transmission mechanism of electric toothbrush by providing a cam mechanism and a crank mechanism in the handle of the present toothbrush. The cam mechanism of the present invention comprise a cam, mounted on a rotary shaft of a motor via a frame; and a slave unit making a reciprocating movement, defined within the handle and engaged with the cam. The crank mechanism of the present invention comprises a crank, mounted concentrically with the brush head; a link rod, jointed with the crank; and a block, defined within the brush body and engaged with the slave unit. A push spring is provided inside the brush body for pressing against the block. An extension spring is provided on the link rod for going through a dead center of the near-end of the crank mechanism. Alternatively, the block is defined as an uneven shape so that an unbalance pressure can act on it to make the link rod go through a dead center of near-end easily. The cam is a cylindrical cam and is respectively provided with two wave crests and two wave hollows that are fixed with the frame. At least one of the wave hollows is provided to depart a pre-determined distance from the frame for going through the dead center of the far-end of the crank mechanism. Furthermore, the link rod of the crank mechanism may be integrated with the slave unit of said cam mechanism. The present invention preferably arranges several groups of brush to be star shape in order to increase the covered area for super cleaning the teeth and the present invention can also super clean the teeth by inclining the surface of the brush head.

In accordance with an aspect of the present invention, the structure of electric brush tooth is simplified as the cam mechanism is cooperated with the crank, thus its cost can be reduced accordingly. Meanwhile, abrasion of the transmission mechanism is less down.

In accordance with another aspect of the present invention, the present invention achieves energy saving and protects the environment against pollution.

In accordance with another aspect of the present invention, the brush head of the present invention formed star shape not only improves the area of contact for super cleaning but also remains space to be convenient for removing the deposit on the teeth.

BRIEF DESCRIPTION OF THE DRAWINGS

With reference to the following drawings, the preferred embodiments of the present invention shall be illustrated in detail.

FIG. 1 is a schematic plan for an electric toothbrush of the prior art, showing a gear box respectively coupled with a motor and a brush head;

FIG. 2 is a perspective view for a brush head of an electric toothbrush of the prior art, on which plenty of groups of brush is formed to be a circle shape;

FIG. 4A is a cross-sectional view in longitudinal direction of the present electric brush tooth;

FIG. 4B is a cross-sectional view along A—A line, showing that the block is defined as an uneven shape;

FIG. 5 is a assembly diagram for the present crank mechanism being coupled with the present brush head;

FIG. 7A is a schematic plan for the wave hollow of the present cam is 4<departed 2.1188 mm from the frame;

FIG. 7B is a curve diagram showing function relation of the offset variable and angle variable of the present cam mechanism in the position of FIG. 7A;

DETAILED DESCRIPTION OF THE DRAWINGS

Figure 3A:
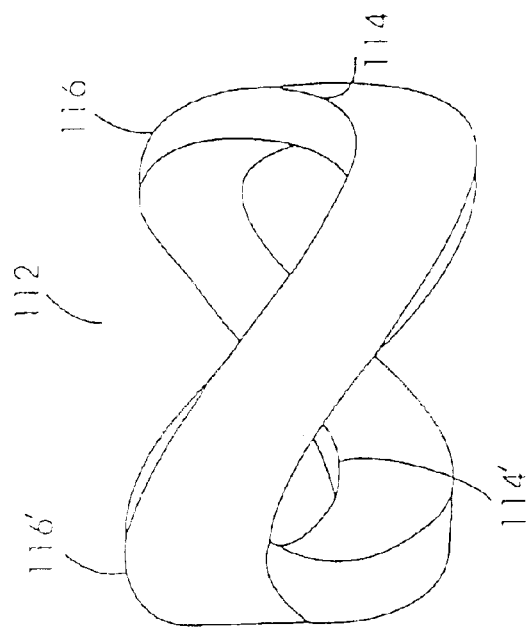
FIG. 3A is a perspective view of a present cam coupled with a motor, which is provided with one wave crest and one wave hollow.
Figure 3B:
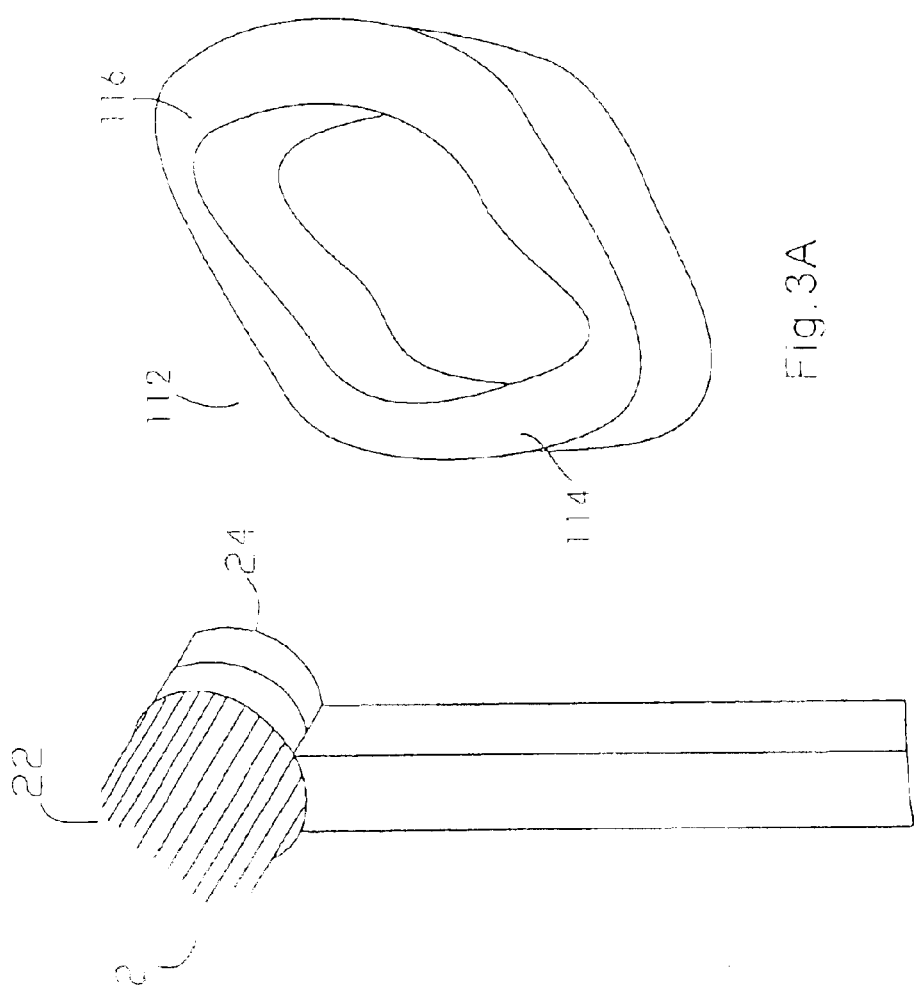
FIG. 3B is a perspective view of another present cam coupled with a motor, which is provided with two wave crests and two wave hollows.

An electronic brush 100 of the present invention firstly applies a cam mechanism 110. The present cam 112 is a cylindrical cam, as shown in FIG. 3A, the cam 112 has one wave hollow 114 and one wave crest 116. In another preferred embodiment, the cam 112 is designed to have two wave hollows 114, 114' and two wave crests 116, 116', as shown in FIG. 3B.

Now referring to FIGS. 4A-4B, the electric brush 100 comprises: a handle 102; a brush body 106, which is mounted with the top end of the handle 102; and, a brush head 300 which is mounted on the top end of the brush body 106. A driver means 101 and the present cam mechanism 110 are provided within the handle 102, wherein wave hollows 114 and 114' of the cylindrical cam 112 are fixed with a frame 118 which is concentrically located to the output shaft 104 of driver means 101. Therefore, the present cylindrical cam 112 can be driven by the driver means 101 to rotate. A slave unit 120 of the present cam mechanism 100 is defined by a pair of supports 105 mounted on the top wall 103, one end of which aligns the circum formed by the wave crests 116, 116' and the wave hollows 114, 114' and the other end of which penetrates the top wall 103 of the handle 102. Thus, the slave unit 120 can cooperate with the cylindrical cam 112 to make a reciprocating movement while the cam 112 rotates.

Therefore, if the cam 112 of the present invention respectively has one wave hollow and one wave crest, the function for offset variable of the slave unit 120 and angle variable of the cam 112 are $$h(\theta) = \tfrac{1}{2} H(1 - \cos \theta) \quad (1)$$

wherein reference h represents offset of the slave unit 120; reference H represents the max offset of the slave unit 120; and reference θ represents turning angle of the cam 112.

If the cam 112 of the present invention respectively has two wave hollows and two wave crests, the function for offset variable of the slave unit 120 and angle variable of the cam 112 are $$h(\theta) = \tfrac{1}{2} H(1 - \cos 2\theta) \quad (2)$$

wherein reference h represents offset of the slave unit 120; reference H represents the max offset of the slave unit 120; and reference θ represents turning angle of the cam 112.

The slave unit 120 is associated with a block 202 of the present crank mechanism 200 provided within the brush body 106. In the same way, the block 202 is also defined by a pair of supports 107 mounted inside the body 200. It is obvious that a spring 210 has to be provided to press the block 202 so that the block 202 can be moved back and forth under the push action of the slave unit 120 and reaction of the spring 210. A link rod 204 is designed on the block 202, thus the link rod 204 will be driven by the block 202. Meanwhile, the link rod 204 is needed to contact with a crank 206. Specifically, the crank 206 is eccentrically provided with a fixed member 208 for hinge joint the link rod 204.

It is the present crank mechanism 200 that drives the bush head 300 to rotate. As shown in FIG. 5, a rotating shaft 304 is provided on a brush head 300 in which the area 306 for fixing several groups of brush 302 are defined in a predetermined shape, such as a circle shape. The rotating shaft 304 penetrates the brush body 106 and is mounted concentrically with the crank 206. Eventually, a brush guard 108 is used for covering the brush body 106 to prevent the crank mechanism 200 from harming the mouth.

With rotating of the driver means 101, the brush head 300 can be driven by the transmission mechanism. Obviously, the turning position of the brush head 300 will be in relation with that of the cam 112. Referring to FIGS. 6A-6H, let's divide the circum formed by wave hollows 114, 114' and wave crests 116, 116' into eight equation, and mark the positions of wave hollows to be Position 1 and Position 5; mark the positions of wave crests 116, 116' to be Position 3 and Positing 7. So the angular interval between the Position 1 to the Position 8 will be 45 degree in turn.

Figure 6A:
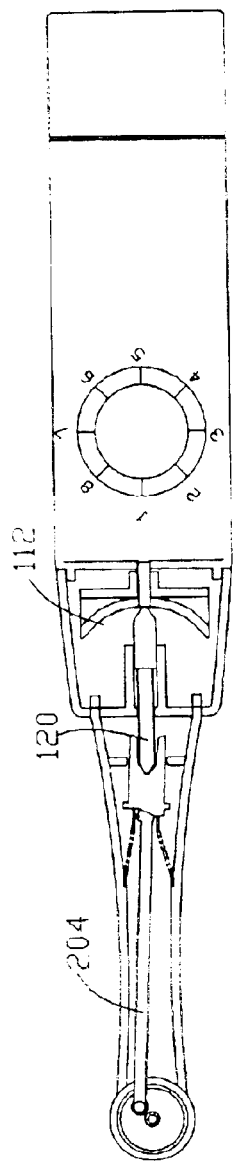
FIGS. 6A-6H are schematic diagram of cooperation for the present crank mechanism and cam mechanism.

At first stage, while the slave unit 120 acts on the Position 1 of the cam 112, the link rod 204 is designed to part from the central line, as shown in FIG. 6A. Let's suppose that, in the initial position, the angle between the abscissa and the line for the fixed member 208 and the center is α.

Figure 6B:
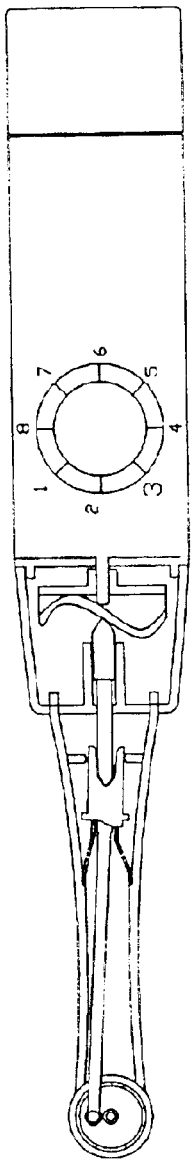

At second stage, the cam 112 moves to Position 2, the slave unit 120 moves forwards to push the block 202 and compresses the spring 210, then the crank 206 will turn 90°-α, as shown in FIG. 6B.

Figure 6C:
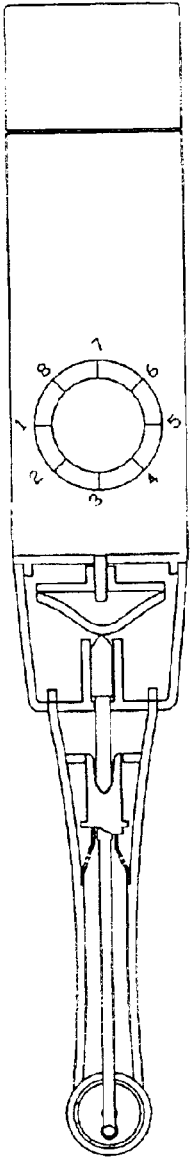

Then at the third stage, the cam 112 will move to Position 3, one of wave crests, and push the slave unit 120 to achieve the max distance. The spring 210 is kept in being compressed and the crank 206 will turn 180°-α, as shown in FIG. 6C.

Figure 6D:
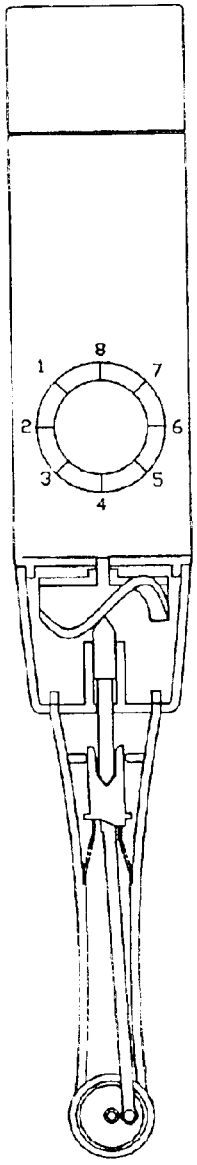

At the fourth stage, the cam 112 moves to Position 4, the elastic force of the spring 210 will act on the block 202 and will push the slave unit 112 moves backwards. So the crank 206 will continuously turn 270°-α, as shown in FIG. 6D.

Figure 6E:
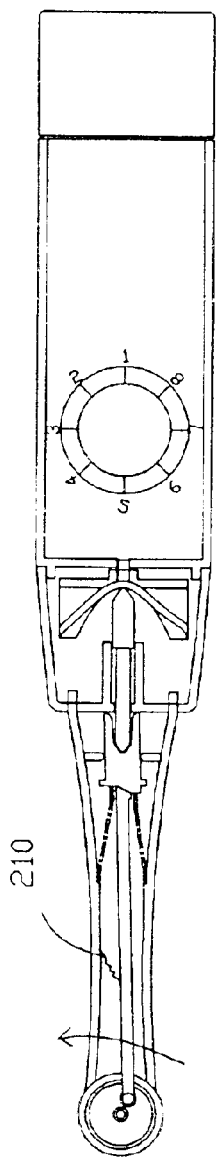

At the fifth stage, the cam 112 moves to Position 5, the other of wave hollows, the crank 210 will turns 360°-2α, as shown in FIG. 6E.

Figure 6F:
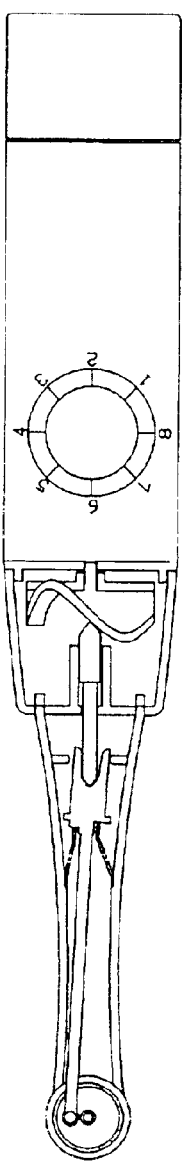

At the sixth stage, the cam 112 moves to Position 6, the movement of slave unit 120 will repeat process of the second stage. Furthermore, the link rod 204 needs to overcome the bottom end, one dead center. So the crank 206 will turns 450°-α, as shown in FIG. 6F.

Figure 6G:
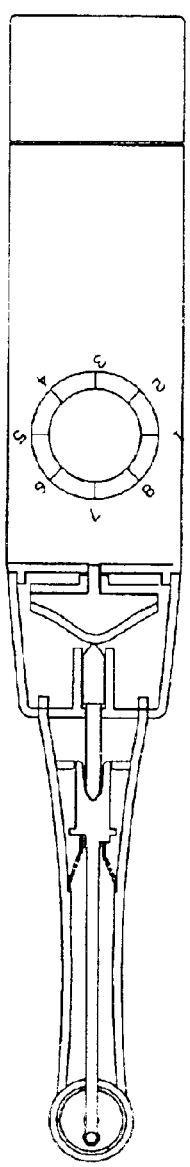
Figure 6H:
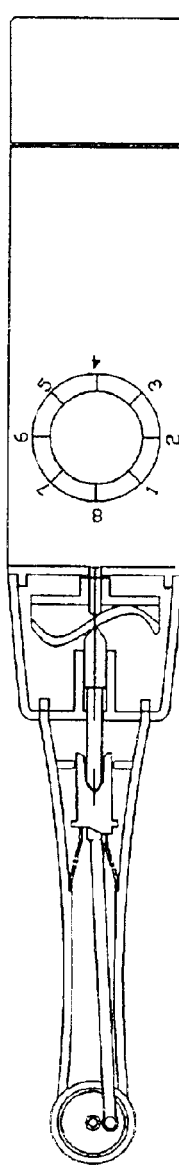

At the seventh stage, the cam 112 will move to Position 7, the other of wave crests, and the crank 206 will turn 540°-α, as shown in FIG. 6G.

At the eighth stage, the cam 112 will move to Position 8, and the crank will turn 630°-α.

Eventually, the cam 112 will return Position 1, the initial position shown in FIG. 6A, to complete one periodic time. The crank 206 will turn 720°, that is, the brush head 300 mounted on the crank 206 will rotate two turns. Obviously, if the cam 112 is provided with one wave crest and one wave hollow, while the cam 112 operating one periodic time, the brush head 300 will rotate one turn.

In fact, when the slave unit 120 achieves two wave hollows and two wave crests, the link rod 206 will be respectively in the dead centers of near end and far end. In order to ensure that the present crank 206 can be operated smoothly, an extension spring 210 is provided on the link rod 204 in an embodiment of the present invention. So the tension force of the spring 210 will help the link rod 204 go through the dead center of near end. Alternatively, in another embodiment, the block 202 is defined as an uneven shape, as shown in FIG. 4B; the lower side of the block 202 protuberates. Definitely, an unbalance pressure will act on the block 202, that is, the pressure of spring 210 on the lower side is higher so that the link rod 204 can go through the dead center of near end easily.

Meanwhile, the present invention is also considered to overcome the dead center of far end. As shown in FIG. 7A-7B, one of wave hollows, such as position 1, is designed to depart 2.1188 mm from the frame 118. This design will certainly change initial angle α between the abscissa and the line for the fixed member 208 and the center and will be helpful for the link rod 204 to go through the dead center of the far end. If so, the brush head will turn one cycle and plus 240 degree totally, i.e. 600 degree.

Figure 8A:
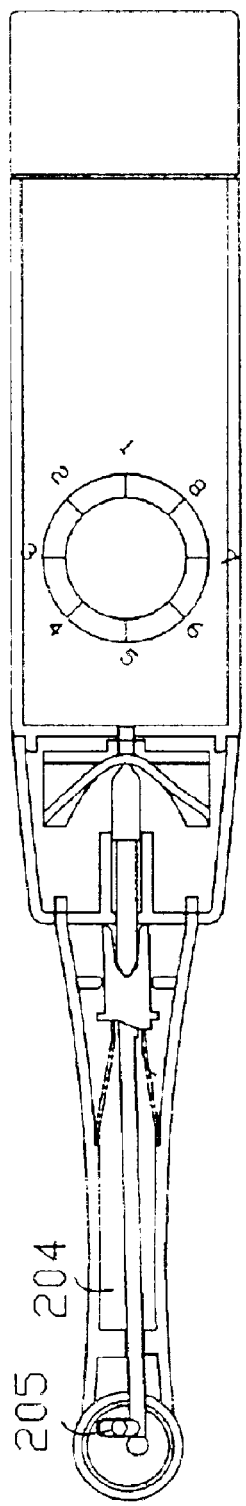
FIG. 8A is another schematic diagram of cooperation for the present crank mechanism, showing a stopper is provided on the link rod.
Figure 8B:
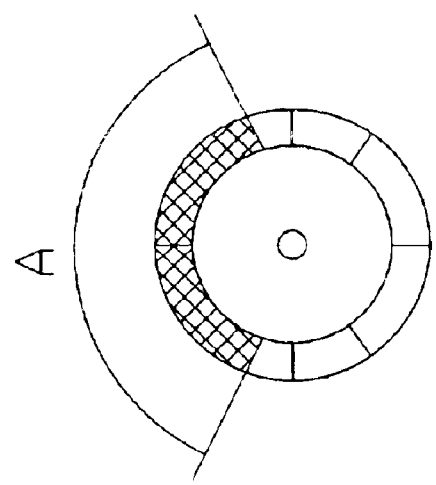
FIG. 8B shows the movement area of the brush head of FIG. 8A.

Availability, if the brush head is permitted rotating in pre-determined area in accordance with the present invention, thus it can avoid the dead center naturally. Referring to FIG. 8A, a stopper 205 is designed on the link rod 204 and is defined in the brush body 106. Obviously, the crank 206 as well as the concentrically mounted flu head brush 300 will move within shadow zone A, as shown in FIG. 8B.

In another embodiment of the present transmission mechanism, the link rod 204 of the crank mechanism 200 is integrated with the slave unit 120 of the cam mechanism 100.

Figure 9:
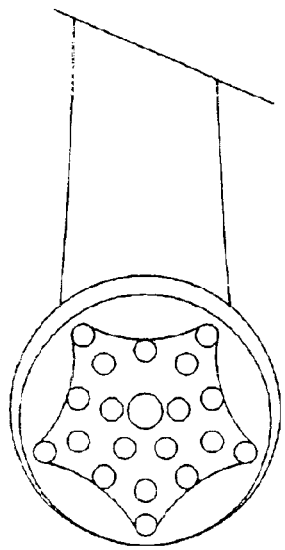
FIG. 9 is a plan view of an embodiment of the present brush head, on which plenty of groups of brush is formed to be star shape.

Preferably, the area 306 of the present brush head 300 for fixing several groups of brush is designed as to be star shape, as shown in FIG. 9, as this design can remain much space 308 for being convenient to remove the deposit on the teeth.

Figure 10:
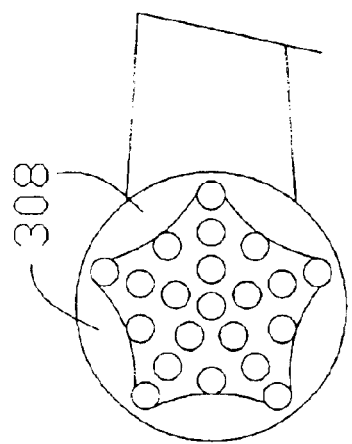
FIG. 10 is a plan view of another embodiment of the present brush head, in which the groups of brush is arranged eccentrically from the brush head.

In another embodiment, the area 306 for fixing several groups of brush is eccentrically arranged from the brush head 300 in order to increase the oscillating angle of brush 302. As shown in FIG. 10, the distance between the center of the area 306 and that of head is about 0.2–1 mm.

Figure 11A:
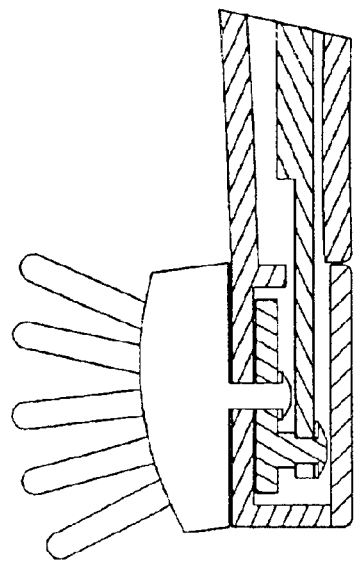
FIG. 11A is a cross-sectional view of another embodiment of the present brush head, in which the brush head is inclined to the brush body.
Figure 11B:
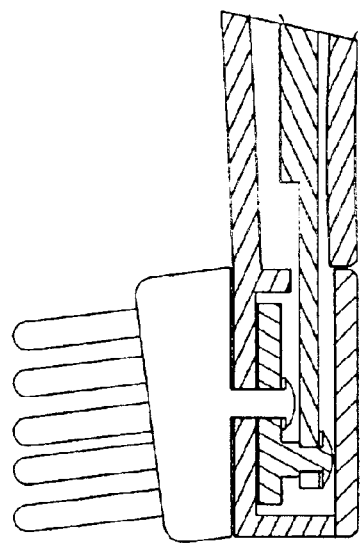
FIG. 11B is a cross-sectional view of further embodiment of the present brush head, in which the inclined surface of the head brush is designed to be a cambered surface.

In further embodiment, the surface of the brush head 300 is designed to incline for increasing the oscillating angle as well, as shown in FIG. 11A. Preferably, the inclination for the surface is about 3–7 degree. However, it is much better for the surface is cambered in order to increase the contact area, as shown in FIG. 11B.

While the invention herein has been described by means of specific embodiments, numerous modifications and variations could be made thereto by those skilled in the art without departing from the scope of the invention set forth in the claims.

What is claimed is:

1. An electric toothbrush comprising
    a brush head for fixing several groups of brush arranged in a pre-determined shape;
    a handle;
    a driver element mounted within said handle;
    a brush body used for mounting said brush head;
    a brush guard used for covering said brush body;
    a cam mechanism, being provided with
        a cam mounted on a rotary shaft of said driver element via a frame; and
        a slave unit making a reciprocating movement, defined within said handle and engaged with said cam;
    a crank mechanism being provided with
        a crank mounted concentrically with said brush head;
        a link rod joined with said crank; and
        a block defined within said brush body and engaged with said slave unit wherein a push spring is provided inside said brush body for pressing against said block.

2. An electric toothbrush according to claim 1, wherein said block is defined as an uneven shape for going through a dead center of a near-end of said crank mechanism.

3. An electric toothbrush according to claim 1, wherein an extension spring is provided on said link rod for going through a dead center of a near-end of said crank mechanism.

4. An electric toothbrush according to claim 3, wherein said link rod of said crank mechanism is integrated with said slave unit of said cam mechanism.

5. An electric toothbrush according to claim 1, wherein a stopper is designed on said link rod for defining said crank to rotate within a pre-determined zone.

6. An electric toothbrush according to claim 1, wherein said cam is a cylindrical cam.

7. An electric toothbrush according to claim 2, wherein said cam is provided with at least a wave crest and at least a wave hollow respectively and at least one of said wave hollows is provided to depart a pre-determined distance from said frame for going through th a dead center of the a far end of said crank mechanism.

8. An electric toothbrush according to claim 3, wherein said several groups of brush are arranged to be star shape.

9. An electric toothbrush comprising
    a brush head for fixing several groups of brush arranged a pre-determined shape;
    a handle;
    a driver element mounted within said handle;
    a brush body used for mounting said brush head;
    a brush guard used for covering said brush body;
    a cam mechanism being provided with
        a cam mounted on a rotary shaft of said driver element via a frame, wherein said cam is a cylindrical cam and is provided with at least a wave crest and at least a wave hollow respectively; and
        a slave unit making a reciprocating movement, defined within said handle and engaged with said cam;
    a crank mechanism being provided with
        a crank mounted concentrically with said brush head;
        a link rod joined with said crank;
        a block defined within said brush body and engaged with said slave unit.

10. An electric toothbrush comprising
    a brush head;
    several groups of brush arranged in a pre-determined shape, which is eccentrically arranged about said brush head;
    a handle;
    a driver element mounted within said handle:
    a brush body used for mounting said brush head;
    a brush guard used for covering said brush body;
    a cam mechanism being provided with
        a cam mounted on a rotary shaft of said driver element via a frame; and
        a slave unit making a reciprocating movement, defined within said handle and engaged with said cam;

a crank mechanism being provided with
- a crank mounted concentrically with said brush head;
- a link rod joined with said crank;
- a block defined within said brush body and engaged with said slave unit, wherein a push spring is provided inside said brush body for pressing against said block.

11. An electric toothbrush according to claim 10, wherein said block is defined as an uneven shape for going through a dead center of a near-end of said crank mechanism.

12. An electric toothbrush according to claim 10, wherein an extension spring is provided on said link rod to be used for going through dead centers of said crank mechanism.

13. An electric toothbrush according to claim 10, wherein said cam is a cylindrical cam.

14. An electric toothbrush according to claim 10, wherein said link rod of said crank mechanism is integrated with said slave unit of said cam mechanism.

15. An electric toothbrush according to claim 10, wherein said several groups of brush are arranged to be star shape.

16. An electric toothbrush comprising
- a brush head, a surface of which is designed as an incline;
- several groups of brush arranged a pre-determined shape;
- a handle;
- a driver element mounted within said handle;
- a brush body used for mounting said brush head;
- a brush guard used for covering said brush body;
- a cam mechanism being provided with
  - a cam mounted on a rotary shaft of said driver element via a frame; and
  - a slave unit making a reciprocating movement defined within said handle and engaged with said cam;
- a crank mechanism, being provided with
  - a crank mounted concentrically with said brush head;
  - a link rod joined with said crank;
  - a block defined within said brush body and engaged with said slave unit wherein a push spring is provided inside said brush body for pressing against said block.

17. An electric toothbrush according to claim 16, wherein said block is defined as an uneven shape for going through a dead center of the near-end of said crank mechanism.

18. An electric toothbrush according to claim 16, wherein said cam is a cylindrical cam.

19. An electric toothbrush according to claim 16, wherein said link rod of said crank mechanism is integrated with said slave unit of said cam mechanism.

20. An electric toothbrush according to claim 16, wherein the incline angle of said surface of said brush head is about 0.5–5 degree.

21. An electric toothbrush according to claim 20, wherein said surface of said brush head is a cambered surface.

22. An electric toothbrush according to claim 21, wherein said several groups of brush are arranged to be star shape.

23. An electric toothbrush comprising
- a brush head, a surface of which is designed as an incline;
- several groups of brush arranged in a pre-determined shape;
- a handle;
- a driver element mounted within said handle;
- a brush body used for mounting said brush head;
- a brush guard used for covering said brush body;
- a cam mechanism being provided with
  - a cam mounted on a rotary shaft of said driver element via a frame; and
  - a slave unit making a reciprocating movement defined within said handle and engaged with said cam;
- a crank mechanism, being provided with
  - a crank mounted concentrically with said brush head;
  - a link rod joined with said crank;
  - a block defined within said brush body and engaged with said slave unit, wherein an extension spring is provided on said link rod to be used for going through dead centers of said crank mechanism.

* * * * *

UNITED STATES PATENT AND TRADEMARK OFFICE
CERTIFICATE OF CORRECTION

PATENT NO. : 6,836,918 B1
DATED : January 4, 2005
INVENTOR(S) : Wong

It is certified that error appears in the above-identified patent and that said Letters Patent is hereby corrected as shown below:

Column 6,
Line 29, after "through" delete "th" and after "of" delete "the".
Line 31, delete "3" and substitute -- 1 --.
Line 60, delete ":" and substitute -- ; --.

Signed and Sealed this

Fourteenth Day of February, 2006

JON W. DUDAS
*Director of the United States Patent and Trademark Office*